(12) United States Patent
Tanaami

(10) Patent No.: US 7,521,024 B2
(45) Date of Patent: Apr. 21, 2009

(54) MAGNETIC BEAD-BASED MIGRATION APPARATUS

(75) Inventor: Takeo Tanaami, Musashino (JP)

(73) Assignee: Yokogawa Electric Corporation, Musashino-shi (JP)

(*) Notice: Subject to any disclaimer, the term of this patent is extended or adjusted under 35 U.S.C. 154(b) by 1485 days.

(21) Appl. No.: 10/098,427

(22) Filed: Mar. 18, 2002

(65) Prior Publication Data

US 2002/0137226 A1    Sep. 26, 2002

(30) Foreign Application Priority Data

Mar. 26, 2001    (JP) .............................. 2001-087292

(51) Int. Cl.
*G01N 33/00*    (2006.01)

(52) U.S. Cl. .................. 422/149; 422/50; 422/68.1; 422/82.01

(58) Field of Classification Search ................ 436/501, 436/514, 515, 516, 523, 326, 184, 172; 422/68.1, 422/82.05, 82.08, 101, 50, 82.01, 149; 210/695, 210/222
See application file for complete search history.

(56) References Cited

U.S. PATENT DOCUMENTS 5,653,859 A  *  8/1997  Parton et al. ................. 204/450

OTHER PUBLICATIONS

T. Tanaami; U.S. Appl. No. 09/562,371, filed May 1, 2000.

* cited by examiner

*Primary Examiner*—Sam P Siefke
(74) *Attorney, Agent, or Firm*—Westerman, Hattori, Daniels & Adrian, LLP.

(57) ABSTRACT

This invention relates to a method to make biopolymers such as proteins or nucleic acids migrate by applying a spatially distributed magnetic field to a solution containing biopolymers marked with magnetic beads. In this case, marking the biopolymers to be fractionated with magnetic beads of different sizes or materials causes different migration speeds and thus causes different positions of the biopolymers after migration. Molecules to be fractionated can be separated in such a manner as mentioned above.

10 Claims, 3 Drawing Sheets

Well 11
10 Separator

21 Stic magnet
10 Separator

MAGNETIC BEAD-BASED MIGRATION APPARATUS

BACKGROUND OF THE INVENTION

1. Field of the Invention

The present invention relates to a migration method and apparatus for the method, that can make biopolymers such as proteins or nucleic acids migrate corresponding to their types.

2. Description of the Prior Art

Electrophoresis has been well known as a method for separating and identifying biopolymers such as proteins or nucleic acids.

However, electrophoresis requires treatment using sodium dodecyl sulfate (SDS) or the like because proteins to be fractionated are not necessarily charged. In such pretreatment, however, there is a problem that particles to be fractionated (proteins) are denatured.

SUMMARY OF THE INVENTION

The objectives of the present invention are as follows: to solve the above problem, and to provide a magnetic bead-based migration method and apparatus for the method, that can make biopolymers such as proteins or nucleic acids easily migrate by only applying a magnetic field to the biopolymers, which are marked with magnetic beads, that facilitates pretreatment, and that is not in danger of causing denaturation of the particles to be fractionated.

In order to achieve such purposes, the invention described in claim 1 is characterized:

such that the method makes biopolymers migrate corresponding to the distribution of a magnetic field having a spatial intensity distribution, by applying such a magnetic field to a solution containing the biopolymers to be fractionated, marked with magnetic beads of different sizes or materials.

In this invention, a spatially distributed magnetic field is applied to a solution containing the biopolymers to be fractionated, the biopolymers being marked with magnetic beads. The magnetic beads migrate together with the biopolymers, as magnetic forces act on the magnetic beads as a result of applying a magnetic field. In this case, differences in migration speeds corresponding to the sizes or materials of magnetic beads are generated, causing differences of positions of biopolymers after migration. In such a manner, molecules to be fractionated are separated.

In addition, treatment for marking the biopolymers to be fractionated with magnetic beads is simple, similar to SDS treatment or the like in electrophoresis, and does not cause denaturation of the molecules to be fractionated.

The invention described in claim 2 relates to a magnetic beads migration apparatus that fractionates the biopolymers to be fractionated placed on the separator corresponding to their types, and is characterized by comprising:

a magnetic field generator that applies a magnetic field having a spatial intensity distribution to a solution containing the above biopolymers marked with magnetic beads of different sizes or materials, and a detector that detects the spatial positions of biopolymers or magnetic beads in the separator, which have migrated corresponding to the distribution of the above applied magnetic field.

A magnetic field generator applies a magnetic field having a spatial intensity distribution to a solution containing the above biopolymers marked with magnetic beads. This causes the biopolymers to move together with the magnetic beads. However, differences in moving speed (migration speed) occur because of differences in the sizes or materials of the magnetic beads, and the biopolymers are developed on the separator.

In this case, as described in claim 3, the applied magnetic field may also be made to have a ramp distribution, such as monotonously increasing or decreasing, in the space where the biopolymers to be fractionated are placed.

In addition, as described in claim 4, the magnetic field generator may also sweep the magnetic field against the above separator, without having a fixed magnetic field.

In this case, the above magnetic beads and molecules to be fractionated are devised so as to be able to migrate, by being placed in a polymer gel as described in claim 5.

In order to detect the positions of molecules to be fractionated after migration, the detector can be configured so that molecule positions are detected using fluorescence from fluorescent molecules or using radioactive materials with which the molecules to be fractionated have been labeled as described in claim 6.

Further, the detector can also be configured to detect the time when the molecules to be fractionated pass by the specialized position during migration using fluorescent or radioactive materials as described in claim 7.

Marking the molecules to be fractionated with magnetic beads is performed in practice by covalent bonding or ionic bonding as described in claim 8. Otherwise, the molecules to be fractionated can also be marked with magnetic beads by preliminarily bonding the above molecules and the magnetic beads with streptoavidin and biotin respectively and then bonding that streptoavidin and biotin as described in claim 9.

Further, the applied magnetic field can be applied so that the molecules to be fractionated marked with magnetic beads can be developed one-dimensionally or two-dimensionally through migration as described in claim 10. Specifically, in the case of two-dimensional development, it should be applied to the separator (chip) of size 1 cm$^2$ or less as described in claim 11.

DESCRIPTION OF THE PREFERRED EMBODIMENTS

Figure 1:
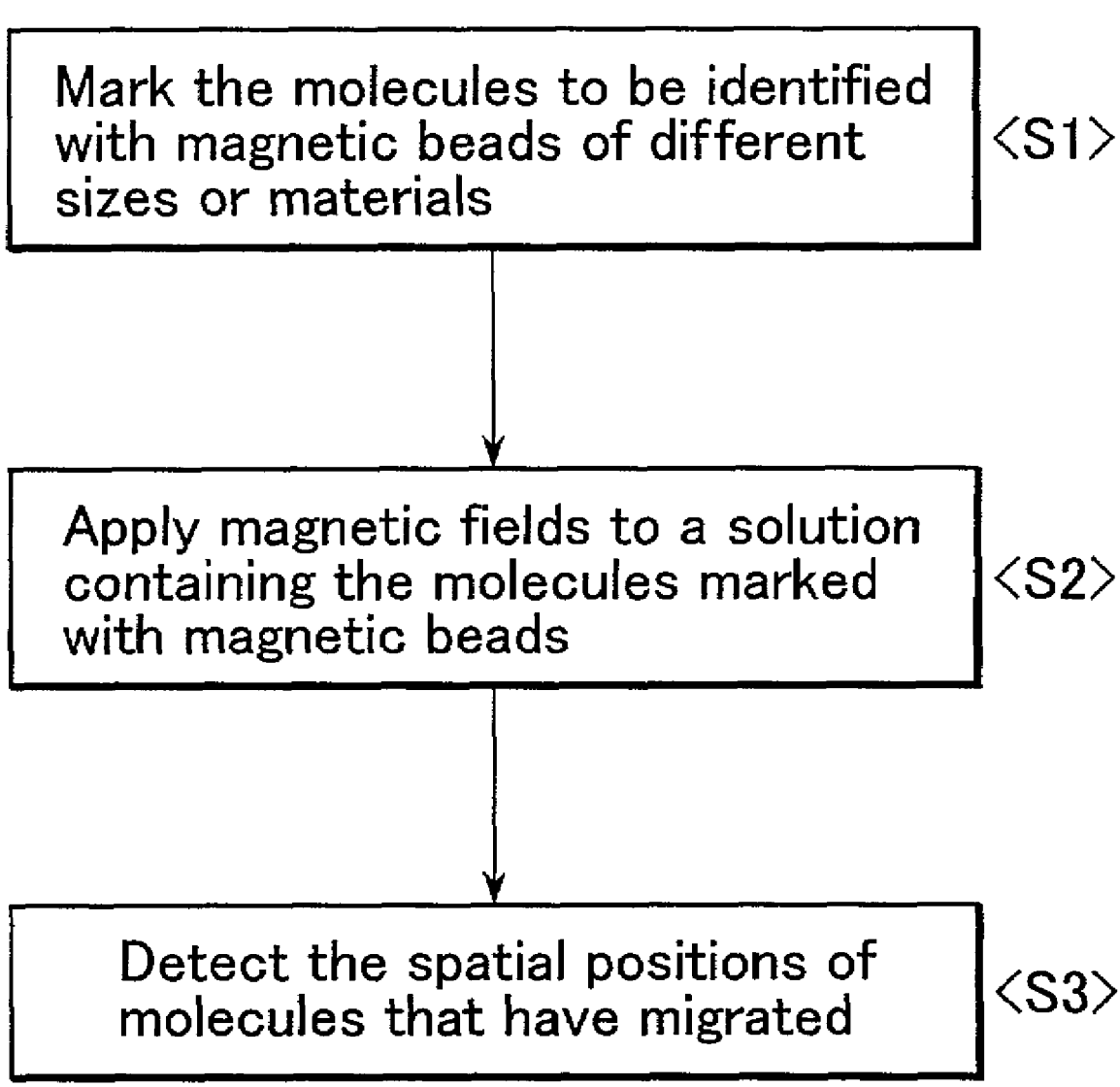
FIG. 1 shows a flow chart for the magnetic beads migration method of the present invention.

The present invention will be hereafter described in detail using drawings. FIG. 1 shows flow chart for the magnetic beads migration method of the present invention. The description will proceed in the order of processes.

(1) Biopolymers to be fractionated are marked with magnetic beads of different sizes or materials corresponding to their types (Step S1).

The migration speed during magnetic migration varies due to the differences in magnetic bead sizes or materials.

For marking the biopolymers with magnetic beads, well-known techniques of covalent bonding, ionic bonding, bonding using streptoavidin and biotin, or the like can be used.

Figure 2:
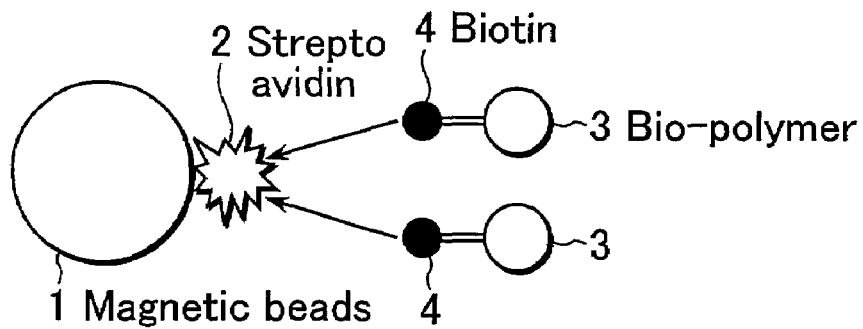
FIG. 2 is a drawing illustrating bonding using streptoavidin and biotin.

Further, a covalent bond is a bond in which an electron of the biopolymer and the magnetic bead is held in common as is well known, and the ionic bond is a bond based on an electrostatic attraction between the biopolymers and the magnetic beads. Bonding using streptoavidin and biotin is a system for marking the biopolymers with magnetic beads, where streptoavidin 2 is preliminarily bonded to the magnetic beads 1, and biotin 4 is bonded to biopolymers 3 respectively and then streptoavidin is bonded to biotin, as shown in FIG. 2.

(2) A magnetic field having a spatial intensity distribution is applied to a solution containing biopolymers marked with magnetic beads (Step S2).

(3) The spatial positions of magnetic beads that have migrated corresponding to the distribution of applied magnetic field are detected (Step S3).

As described above, the biopolymers to be fractionated can be separated and identified by making the biopolymers migrate. In this case, since SDS treatment or the like that was carried out in conventional electrophoresis as a pretreatment is not employed, denaturation of biopolymers does not occur.

Figure 3:
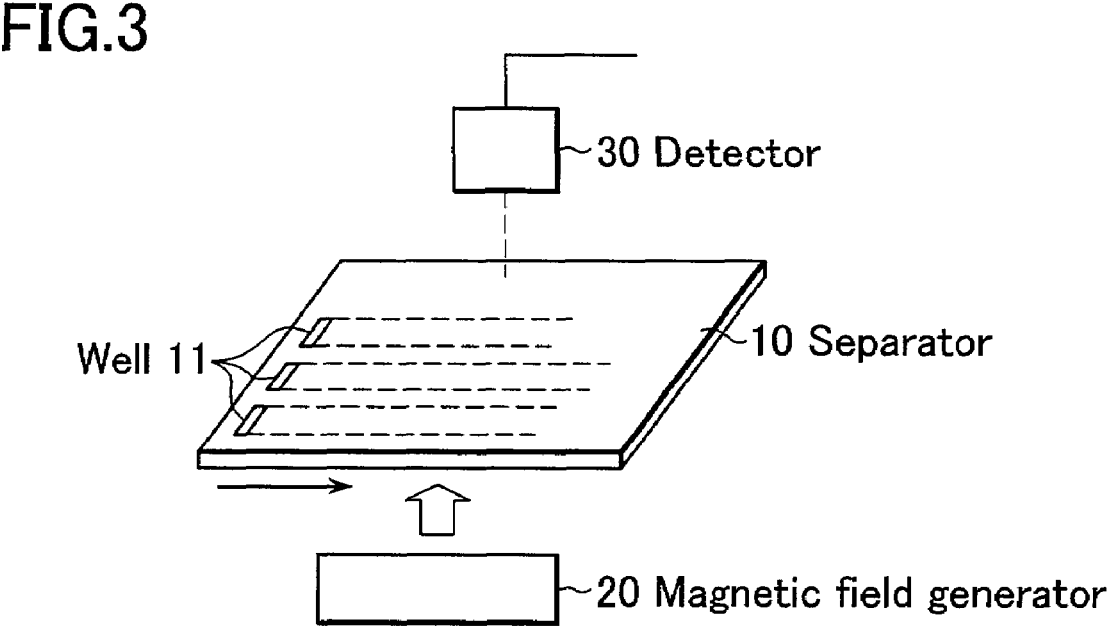
FIG. 3 is a drawing indicating the configuration of an essential portion of an embodiment for an apparatus to realize the magnetic bead-based migration method of the present invention.

FIG. 3 is a drawing indicating the configuration of an essential portion of an embodiment for an apparatus to realize the magnetic bead-based migration method of the present invention. The magnetic bead-based migration apparatus of the present invention consists of separator 10, magnetic field generator 20, and detector 30.

Solution containing biopolymers is poured into each well 11 on separator 10. Each biopolymer is marked with magnetic beads of different sizes or masses or the like respectively through pretreatment.

Figure 4:
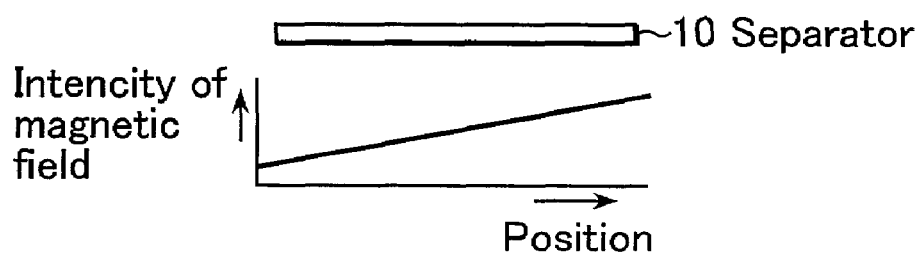
FIG. 4 is a drawing indicating an example of magnetic intensity distribution.

Magnetic field generator 20 applies a magnetic field having a spatial intensity distribution to separator 10 (that is, to a solution containing biopolymers marked with magnetic beads). The magnetic field intensity distribution is, for example, a ramp distribution that gradually increases corresponding to the migrating direction of separator 10 as shown in FIG. 4. Such a magnetic field can, for example, be generated using electromagnetic coils or permanent magnets or the like.

Detector 30 detects the spatial positions (moved positions) of particles to be fractionated marked with magnetic beads when the biopolymers migrate corresponding to the distribution of the magnetic field. For example:

a system where the spatial positions are detected by detecting fluorescence emitted by irradiation of excitation light with particles to be fractionated marked with fluorescent molecules, or a system where the spatial positions are known by detecting radioisotopes (RI) that are preliminarily stuck to the particles to be fractionated, or the like is used.

Actions in such a configuration will be described below. First, mark the molecules (biopolymers) to be fractionated with magnetic beads of different sizes or materials in advance.

In order to mark the particles to be fractionated with magnetic beads, a well-known bonding technique can be used such as covalent bonding, ionic bonding, or bonding of streptoavidin to biotin.

Figure 5:
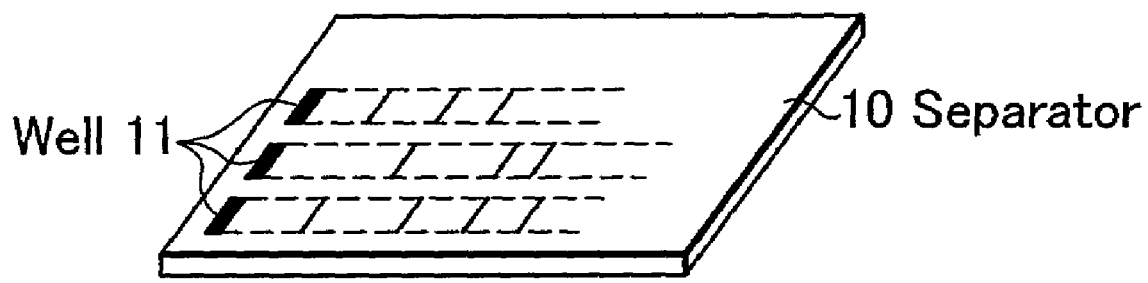
FIG. 5 is a drawing illustrating separation of molecules by magnetic migration.

Solution containing particles to be fractionated marked with magnetic beads through such pretreatment is poured into wells 11 on separator 10. When a magnetic field is generated by magnetic field generator 20 and applied, magnetic beads bonded to the particles to be fractionated are attracted by magnetic force, move in the polymer gel and are separated as shown in FIG. 5. The speeds or positions of movement are different corresponding to the sizes or materials of bonded magnetic beads.

As described above, particles to be fractionated can be identified by detecting the positions of moved particles after migration. Otherwise, particles to be fractionated can be separated and detected by detecting the time when particles pass by the specialized positions. In addition, it is necessary to irradiate excitation light to the particles in the case of detecting particles using fluorescence.

The present invention is not limited to the above embodiments and may include many further changes and versions without departing from the scope of spirit thereof.

Figure 6:
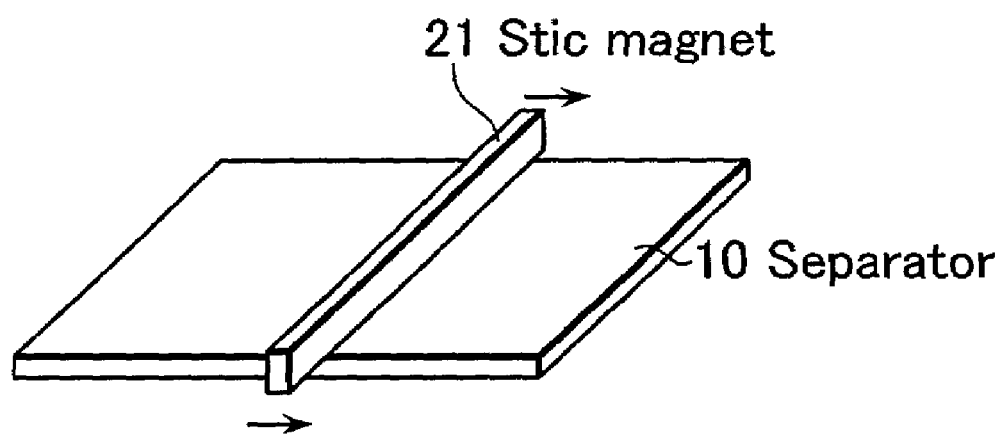
FIG. 6 is a configuration drawing indicating another example of applying a magnetic field.

For example, a constant magnetic field having a spatial intensity distribution is applied in a fixed manner using fixed electromagnetic coils or permanent magnets or the like in the above embodiments. However, the magnetic field may also be swept moving a stick magnet in the migrating direction on separator 10 as shown in FIG. 6.

Further, the distribution of the magnetic field is not limited to a one-dimensional direction but can be devised in two-dimensional directions so that particles to be fractionated marked with magnetic beads are developed on a two-dimensional plane on separator 10. The development on such a two-dimensional plane is most suitable for separators (chips) of 1 $cm^2$ or less.

In addition, the magnetic field may have a ramp distribution, such as monotonously increasing or decreasing, in spaces where particles to be fractionated are placed.

As seen in the above description, according to the present invention, biopolymers such as proteins or nucleic acids can easily be made to migrate by attracting magnetic beads with which the biopolymers have been marked in advance, by applying a magnetic field to the biopolymers.

In addition, the present invention has an advantage that particles to be fractionated are not in danger of causing denaturation because the present invention does not require such SDS treatment as in electrophoresis (electro-migration).

What is claimed is:

1. A magnetic bead-based migration apparatus that fractionates biopolymers to be fractionated placed on a separator corresponding to their types comprising:

a separator having a first surface and a second surface;

a well formed on the first surface of the separator, into which a solution containing biopolymers are poured, the biopolymers being marked with magnetic beads of different sizes or materials;

a magnetic field generator disposed below the second surface of the separator, wherein the magnetic field generator applies a magnetic field having a spatial intensity distribution to the solution, and a detector disposed above the first surface of the separator, wherein the detector detects the spatial positions of the biopolymers or magnetic beads that migrate corresponding to the distribution of said applied magnetic field in the separator.

2. A magnetic bead-based migration apparatus in accordance with claim 1, wherein said applied magnetic field has a ramp distribution, such as monotonously increasing or decreasing, in a space where biopolymers to be fractionated are placed.

3. A magnetic bead-based migration apparatus in accordance with claim 1 or claim 2, wherein said magnetic field generator is configured to be able to sweep an applied magnetic field against said separator.

4. A magnetic bead-based migration apparatus in accordance with claim 1 or claim 2, wherein said magnetic beads and biopolymers to be fractionated are placed in polymer gel so as to be capable of migrating.

5. A magnetic bead-based migration apparatus in accordance with claim 1 or claim 2, wherein said molecules to be fractionated are labeled with fluorescent molecules or radioactive materials and their positions can be determined by detecting fluorescence emitted from the fluorescent molecules or detecting radioactive materials.

6. A magnetic bead-based migration apparatus in accordance with claim 1 or claim 2, wherein:

said molecules to be fractionated are labeled with fluorescent molecules or radioactive materials and said detector can determine the time when said molecules to be fractionated pass by specific positions by detecting fluorescence from the fluorescent molecules or detecting radioactive materials.

7. A magnetic bead-based migration apparatus in accordance with claim 1 or claim 2, wherein said magnetic beads are bonded to molecules to be fractionated through covalent bonding or ionic bonding.

8. A magnetic bead-based migration apparatus in accordance with claim 1 or claim 2, wherein said magnetic beads are bonded to molecules to be fractionated using streptoavidin and biotin, each bonded to the magnetic beads and molecules to be fractionated respectively.

9. A magnetic bead-based migration apparatus in accordance with claim 1 or claim 2, wherein said magnetic field generator applies a magnetic field so that the molecules to be fractionated marked with said magnetic beads are developed in a one-dimensional manner or two-dimensional manner due to migration.

10. A magnetic bead-based migration apparatus in accordance with claim 9, wherein said two-dimensional development is applied to chips of $1\ cm^2$ or less.

\* \* \* \* \*